United States Patent [19]

Mentrup et al.

[11] 3,992,537
[45] Nov. 16, 1976

[54] PHARMACEUTICAL COMPOSITIONS CONTAINING AN N-PHENYL-IMIDAZOLIDINE-2-ONE AND METHOD OF USE

[75] Inventors: Anton Mentrup; Ernst-Otto Renth; Kurt Schromm, all of Ingelheim am Rhein; Peter Danneberg, Ockenheim, all of Germany

[73] Assignee: Boehringer Ingelheim GmbH, Ingelheim am Rhein, Germany

[22] Filed: Dec. 1, 1975

[21] Appl. No.: 636,738

Related U.S. Application Data

[60] Division of Ser. No. 440,823, Feb. 8, 1974, Pat. No. 3,937,708, which is a continuation of Ser. No. 259,532, June 5, 1972, abandoned.

[30] Foreign Application Priority Data

June 7, 1971 Austria .................................. 4920/71

[52] U.S. Cl. .............................................. 424/250
[51] Int. Cl.² ........................................ A61K 31/495
[58] Field of Search .................. 424/250; 260/268 H Primary Examiner—Stanley J. Friedman
Attorney, Agent, or Firm—Hammond & Littell

[57] ABSTRACT

Pharmaceutical compositions containing as an active ingredient a compound of the formula

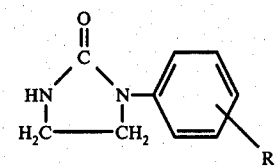

wherein R' is in the m- or p-position and is selected from the group consisting of $$-CH_2-A, -CHR_1-CH_2-A$$

and $$-CHR_1-CH-A,$$
$$\phantom{-CHR_1-}|$$
$$\phantom{-CHR_1-}CH_3$$

where
 $R_1$ is hydrogen or hydroxyl, and
 A is

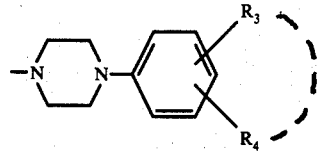

where
 $R_3$ is hydrogen, chlorine, methyl, ethyl, trifluoromethyl or lower alkoxy, and
 $R_4$ is hydrogen or methyl, or
 $R_3$ and $R_4$, together with each other and neighboring carbon atoms of the phenyl ring to which they are attached, are naphthyl,
or a non-toxic, pharmacologically acceptable acid addition salt thereof; and a method of using the same as CNS-depressants, neuroleptics and anticholesteremics.

10 Claims, No Drawings

PHARMACEUTICAL COMPOSITIONS CONTAINING AN N-PHENYL-IMIDAZOLIDINE-2-ONE AND METHOD OF USE

This is a division of copending application Ser. No. 440,823 filed Feb. 8, 1974, now U.S. Pat. No. 3,937,708 granted Feb. 10, 1976; which in turn is a continuation of application Ser. No. 259,532 filed June 5, 1972, now abandoned.

This invention relates to novel pharmaceutical compositions containing an N-phenyl-imidazolidine-2-one or a non-toxic salt thereof, as well as to a method of using the same as CNS-depressants, neuroleptics and anticholesteremics.

More particularly, the present invention relates to novel pharmaceutical dosage unit compositions containing as an active ingredient an N-phenyl-imidazolidine-2-one of the formula

[Structural formula I]

wherein R' is in the m- or p-position and is seleced from the group consisting of $-CH_2-A$,
$-CHR_1-CH_2-A$ and $-CHR_1-CH-A$,
       $|$
       $CH_3$ where
R$_1$ is hydrogen or hydroxyl, and
A is

[Structural formula]

where
R$_3$ is hydrogen, chlorine, methyl, ethyl, trifluoromethyl or lower alkoxy, and
R$_4$ is hydrogen or methyl, or
R$_3$ and R$_4$, together with each other and neighboring carbon atoms of the phenyl ring to which they are attached, are naphthyl, or a non-toxic, pharmacologically acceptable acid addition salt thereof.

A subgenus thereunder is constituted by pharmaceutical dosage unit compositions containing as an active ingredient a compound of the formula I wherein R' is in the m- or p-position and is selected from the group consisting of $-CH_2-A$,
$-CHR_1-CH_2-A$ and $-CHR_1-CH-A$
       $|$
       $CH_3$ where
R$_1$ is hydrogen or hydroxyl, and
A

[Structural formula]

where
R$_3$ is hydrogen, chlorine, methyl or ethyl, and
R$_4$ is hydrogen or methyl, or
R$_3$ and R$_4$, together with each other and neighboring carbon atoms of the phenyl ring to which they are attached, are naphthyl, or a non-toxic, pharmacologically acceptable acid addition salt thereof.

A further subgenus thereunder is constituted by pharmaceutical dosage unit compositions containing as an active ingredient a compound of the formula I, wherein R' is in the m- or p-position and is selected from the group consisting of $-CH_2-CH_2-A$ and $-CH_2-CH-A$,
       $|$
       $CH_3$ where
A is

[Structural formula]

where
R$_3$ is hydrogen, chlorine, methyl or ethyl, and
R$_4$ is hydrogen or methyl, or
R$_3$ and R$_4$, together with each other and neighboring carbon atoms of the phenyl ring to which they are attached, are naphthyl, or a non-toxic, pharmacologically acceptable acid addition salt thereof.

The compounds embraced by formula I above may be prepared by the following methods:

Method A

By reacting an N-substituted piperazine of the formula $$H - A \qquad \qquad II.$$

wherein A has the same meanings as in formula I, with an N-phenyl-imidazolidine-2-one of the formula

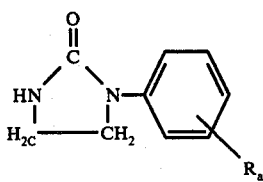

(III)

wherein $R_a$ is —$CH_2$—X, —$CHR_1$—$CH_2$—X or

—$CHR_1$—$\underset{\underset{CH_3}{|}}{CH_2}$—X, each in m- or p-position,
where X is an anion which is capable of combining with the hydrogen atom of the piperazine derivative of the formula II and being split off as an acid of the formula H-X, such as halogen, O—$SO_2$-alkyl or O—$SO_2$—aryl, in the presence of an h-x-binding agent, such as potassium carbonate, sodium carbonate or a sufficient excess of the piperazine derivative of the formula II.

Method B

By subjecting a urea derivative of the formula

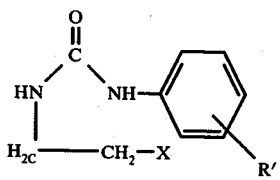

(IV)

wherein R' has the same meanings as in formula I, and X has the meanings defined in formula III, to ring closure through heating in the presence of a strong base, such as potassium hydroxide or sodium hydroxide.

Method C

By subjecting an ethylenediamine derivative of the formula

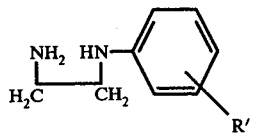

(V)

wherein R' has the same meanings as in formula I, to ring closure with a suitable carbonic acid derivative, especially with phosgene, a chlorocarbonic acid ester, a carbonic acid ester, N,N'-carbonyl-diimidazole or urea, or with a metal cyanate in the presence of an acid.

However, instead of starting from an amine of the formula V, it is also possible to start from an intermediate, such as a carbamate, a urea or a carbamic acid chloride, and subject it to ring closure.

Method D

By reductive amination of an N-phenyl-imidazolidine-2-one of the formula

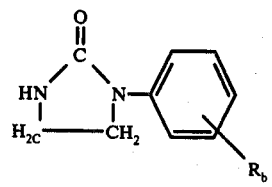

(VI)

wherein
$R_b$ is —CHO, —$CHR_1$, —$C_nH_{2n-1}O$ or —O—$CH_2$—$CHR_1$—$C_nH_{2n-1}O$, each in m- or p-position,
wherein
$R_1$ has the same meanings as in formula I, and
n is 1,2,3, or 4
with a piperazine derivative of the formula II and catalytically activated hydrogen.

Method E

For the preparation of a compound of the formula I wherein R' is —CH(OH)—$CH_2$—A, by reducing a ketone of the formula

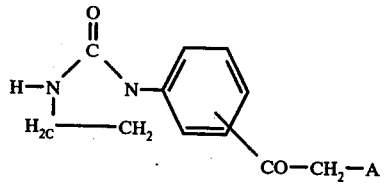

(VII)

wherein A has the same meanings as in formula I, preferably with a complex hydride such as sodium borohydride, or also with catalytically activated hydrogen.

Method F

For the preparation of the formula I where in $R_1$ is hydroxyl. By reacting an N-phenyl-imidazolidine-2-one of the formula

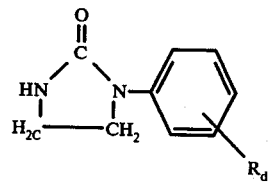

(VIII)

wherein $R_d$ is

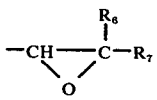

or

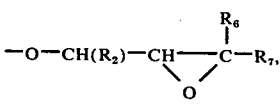

each in m- or p-position,
where $R_6$ and $R_7$ are hydrogen, with a piperazine derivative of the formula II.

Method G

For the preparation of a compound of the formula I wherein $R_1$ is hydrogen, by reacting an N-phenyl-imidazolidine-2-one derivative of the formula

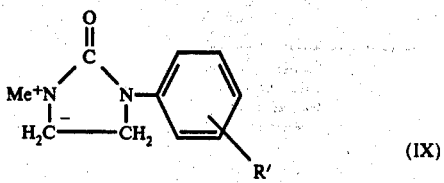

wherein
R' has the same meanings as in formula I, except that R₁ is hydrogen, and
Me⁺ is an alkali metal cation,
with a compound of the formula

H — X    X.

wherein X has the same meanings as in formula III. The compound of the formula IX may be obtained from the corresponding nor-compound by metallization with, for example, sodium hydride, lithium amide, potassium tert. butylate or the like.

The starting compounds needed for methods A through G are either known compounds or may be prepared by conventional methods.

The compounds embraced by formula I occur as racemic mixtures or as optically active isomers, such as antipode pairs or diastereomeric pairs; to the extent that these compounds occur as racemates or diastereomeric antipode pairs, these may be separated in conventional manner into the diastereomeric racemates or the individual optical antipodes.

The optically inactive as well as the optically active forms of the compounds of the formula I are organic bases and therefore form acid addition salts with inorganic or organic acids. Examples of non-toxic, pharmacologically acceptable acid addition salts are those formed with hydrochloric acid, hydrobromic acid, sulfuric acid, methanesulfonic acid, acetic acid, propionic acid, citric acid, maleic acid, tartaric acid, 8-chloro-theophylline or the like.

Wherever or whenever we refer to "lower alkyl" or "lower alkoxy" herein, we intend to include generally those of 1 to 4 and preferably 1 to 2 carbon atoms. Likewise, when we refer to "aryl", we mean preferably phenyl or also naphthyl; "aralkyl" preferably designates benzyl; and chlorine and bromine are preferred meanings of "halogen".

The following examples illustrate the preparation of compounds of the formula I and non-toxic acid addition salts thereof.

EXAMPLE 1

1-[4'-Imidazolidinon-(2')-yl-phenethyl]-4-(3''-chlorophenyl)-piperazine 19.6 gm (0.1 mol) of N-(3-chlorophenyl)-piperazine and 23.0 gm (0.1 mol) of 2-(4'-nitrophenyl)-ethylbromide were refluxed in 150 ml of acetonitrile in the presence of 20 gm of potassium carbonate for two hours. The hot solution was vacuum-filtered, the residue was washed with acetonitrile and the combined solutions were concentrated by evaporation. Treatment of the residue with isopropanol yielded 19 gm of 1-(4'-nitrophenethyl)-4-(3''-chlorophenyl)-piperazine (m.p. 87° C) and 4.5 gm more were obtained from the mother liquor.

The total yield was 23.5 gm (70% of theory). The nitro-compound was dissolved in 240 ml of methanol and hydrogenated in the presence of 1 gm of PtO₂ at 20° C and 5 atmospheres gauge of hydrogen until the nitro group had been reduced. After separation of the catalyst, 21 gm of amine were obtained as a distillation residue, which was reacted without further purification with 8.5 gm of β-chloroethylisocyanate in 150 ml of benzene by heating to 50° C for three hours, yielding 27 gm (96% of theory), of the following compound:

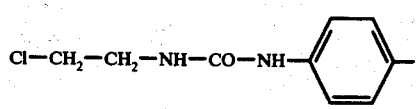

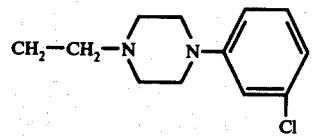

decomposition point above 200° C.

27 gm of this substance were dissolved in 360 ml of hot ethanol, and a solution of 4.0 gm of potassium hydroxide in 40 ml of ethanol was then added. The reaction mixture was refluxed for 3 to 5 minutes and then vacuum-filtered after cooling, and the residue was freed from inorganic matter by extraction with water. 17 gm of the compound of the formula

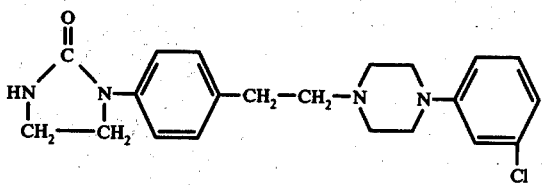

were obtained in the form of the base. For conversion into the salt, the base was heated to boiling in 500 ml of ethanol, and an equivalent quantity of methanesulfonic acid was then added in the form of an ethanolic solution. 20.5 gm of the methanesulfonate, m.p. 239° C (from ethanol), were obtained.

The following compounds were prepared in a manner analogous to that described in Example 1:

TABLE 1

| Example No. | R' | a) Acid/m.p. or decomposition point of the salt [°C]<br>b) M.p. of base [°C] |
|---|---|---|
| 2 | −(CH₂)₂−N(piperazine)N−(2-ethylphenyl) | a) CH₃SO₃H/209<br>b) 180–181 |
| 3 | −(CH₂)₂−N(piperazine)N−(2-methylphenyl) | a) CH₃SO₃H/211<br>b) 195 |
| 4 | −CHOH−CH₂−N(piperazine)N−(2-methylphenyl) | a) CH₃SO₃H/191<br>b) 223 |
| 5 | −(CH₂)₂−N(piperazine)N−(2-chlorophenyl) | a) CH₃SO₃H/263–265 |
| 6 | −(CH₂)₂−N(piperazine)N−(4-chlorophenyl) | a) CH₃SO₃H/241 |
| 7 | −(CH₂)₂−N(piperazine)N−C₆H₅ | a) CH₃SO₃H/271 |
| 8 | −(CH₂)₂−N(piperazine)N−(3-CF₃-phenyl) | a) CH₃SO₃H/216–217 |
| 9 | −CH₂−CH(CH₃)−N(piperazine)N−(2-methylphenyl) | a) HCl/299–301 |
| 10 | −(CH₂)₂−N(piperazine)N−(2,4-dimethylphenyl) | a) CH₃SO₃H/325 |
| 11 | −(CH₂)₂−N(piperazine)N−(3,4-dimethylphenyl) | a) CH₃SO₃H/269–271 |

The common structure shown at the top of the table is:

2-oxo-imidazolidine with HN−CH₂−CH₂−N(−C₆H₄−R') substituent (i.e., 1-(4-R'-phenyl)-imidazolidin-2-one derivatives).

TABLE 1-continued
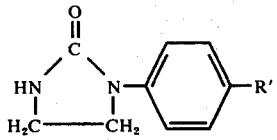
| Example No. | R' | a) Acid/m.p. or decomposition point of the salt [° C]<br>b) M.p. of base [° C] |
|---|---|---|
| 12 | 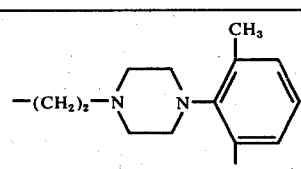 | a) HCl/278–280 |
| 13 | 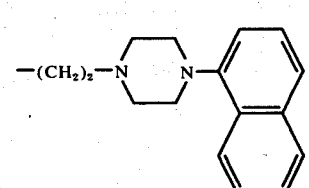 | a) CH$_3$SO$_3$H/235–236 |
| 14 | 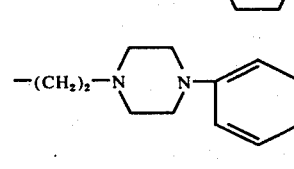 | a) CH$_3$SO$_3$H/295–298 |
| 15 | 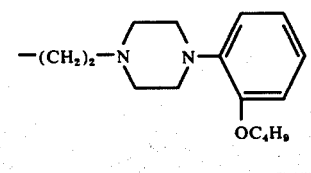 | a) CH$_3$SO$_3$H/202 |
| 16 | 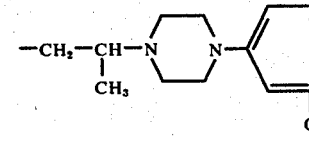 | a) CH$_3$SO$_3$H/236–238 |
| 17 | 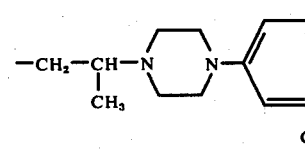 | a) CH$_3$SO$_3$H/300–301 |
| 18 | 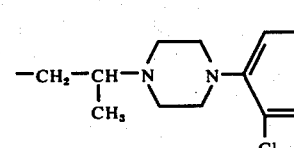 | a) CH$_3$SO$_3$H/218 |
| 19 | 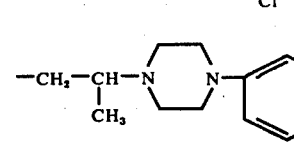 | a) CH$_3$SO$_3$H/275–279 |
| 20 | 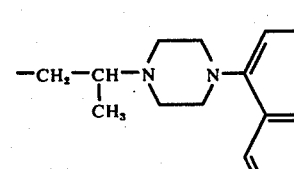 | a) CH$_3$SO$_3$H/270 |

In the following examples, Z denotes the radical

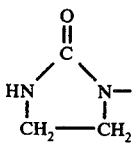

The following compounds were prepared in analogous manner (formula I, R' = as indicated):

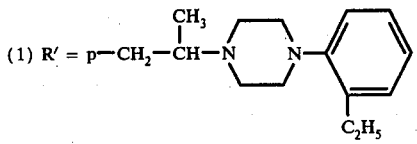

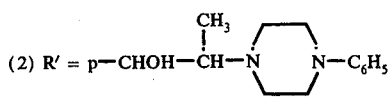

EXAMPLE 21

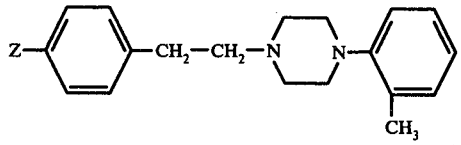 (A)

28.4 gm (0.1 mol) of 2-[4-imidazolidinon-(2)-yl-phenyl]-ethyl methyl sulfonate, obtained from 2-[4-imidazolidinon-(2)-yl-phenyl]-ethanol and methanesulfochloride in pyridine, were reacted with 17.5 gm of N-(2-methylphenyl)-piperazine in 120 ml of acetonitrile in the presence of 21 gm of sodium hydroxide solution by refluxing for one hour. Compound A was isolated as the base, meltingg point 195° C.

The following compounds were prepared in analogous manner (formula I, R' = as indicated):

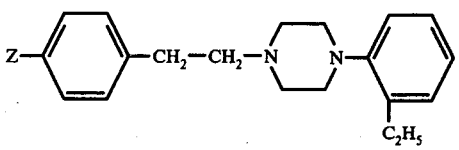

EXAMPLE 23

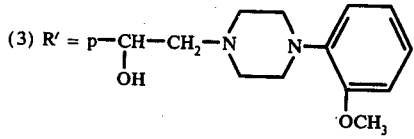 (C)

15.5 gm (0.05 mol) of N-[β-p-aminophenyl)-ethyl]-N'-(o-ethylphenyl-piperazine, 1.6 gm of paraformaldehyde and a solution of 4.1 gm of potassium cyanide in 7 ml of water were combined in 85 ml of glacial acetic acid at 15° to 20° C, and the mixture was allowed to stand overnight at room temperature. The resulting product of the formula

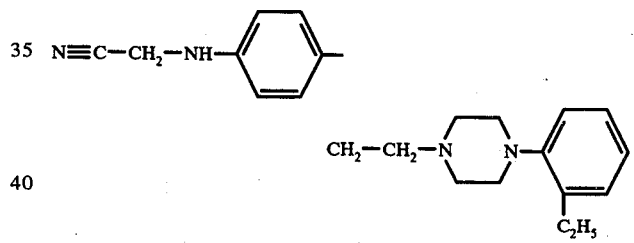

had a melting point of 137°–138° C. It was hydrogenated in methanol, using PtO₂ as the catalyst, to form

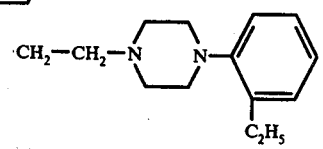

EXAMPLE 22

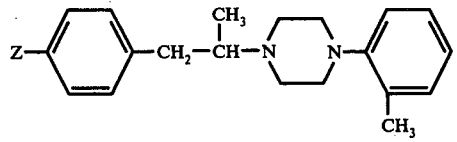 (B)

10 gm of 1-(4'-imidazolidinon-2'-yl-phenyl)-2-oxo-propane were hydrogenated with 8.1 gm of N-(2-methylphenyl)-piperazine in 100 ml of methanol in the presence of 1 gm of PtO₂ at 60° C and 5 atmospheres gauge until the calculated quantity of hydrogen had been taken up. After removal of the catalyst, the methanol was distilled off, and the residue was crystallized by the addition of acetonitrile. The hydrochloride of compound B, which melted at 299°–301° C and crystallized as the monohydrate, was obtained from the base in a small quantity of methanol by adding concentrated hydrochloric acid.

which was treated in benzene with the calculated quantity of N,N'-carbonyldiimidazole dissolved in tetrahydrofuran. The mixture was allowed to stand overnight at room temperature, was then refluxed for two hours, and the resulting product C was isolated as the base (m.p. 178°–181° C).

The following compounds were prepared in analogus manner: (formula I, R' = as indicated)

(1) R' = p—CH$_2$—CH$_2$—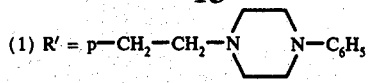

(2) R' = p—CH$_2$—CH$_2$—

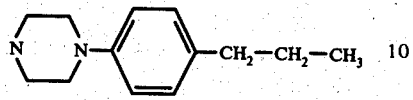

EXAMPLE 24

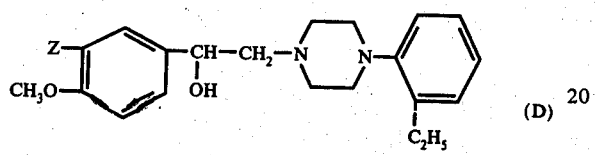
(D)

4-Methoxy-3-nitro-acetophenone was reduced to 4-methoxy-3-amino-acetophenone, which was reacted with β-chloroethyl-isocyanate to form

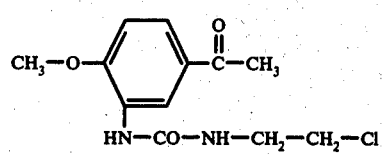

(m.p. 149° C) which was converted into the imidazolidinone derivative of the formula

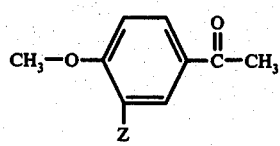

(m.p. 186°–188° C) by reaction with potassium hydroxide in ethanol. Reaction of this compound with bromine in chloroform yielded the compound of the formula

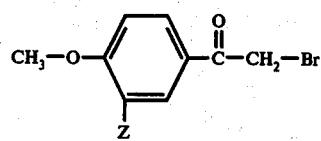

which was reacted as the raw product (85 gm) with 105 gm of N-(2-ethyl-phenyl)-piperazine in 1500 ml of acetonitrile to yield the compound of the formula

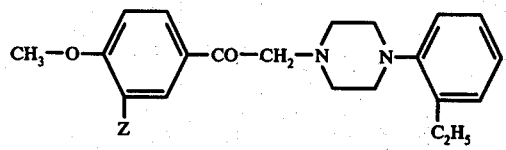

(m.p. 170°–172° C). 5 gm of NaBH$_4$ was added portionwise to 32 gm of this compound in 250 ml of methanol. The reaction mixture was left to stand overnight and was then worked up, yielding 32.5 gm of compound 1 in the form of its hydrochloride (m.p. 234° C).

The following compound was prepared in analogous manner:

EXAMPLE 25

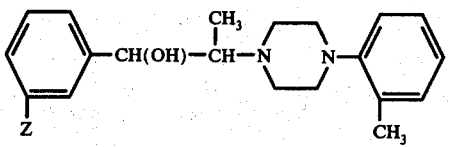

(E, threo- and erythro form)

35 gm of 3-amino-propiophenone in 250 ml of benzene were reacted with 27 gm of β-chloroethyl-isocyanate to yield the compound of the formula

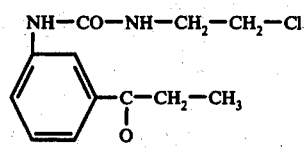

(m.p. 114° C), which was cyclized with potassium hydroxide to form 3-[imidazolidinon-(2')-yl]-propiophenone (m.p. 162° C), which was reacted with bromine in chloroform to yield the bromoketone of the formula

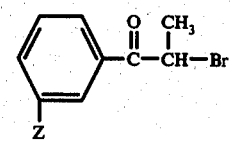

(m.p. 181° C).

33 gm of this bromoketone were boiled with 39 gm of N-(2-methyl-phenyl)-piperazine in 660 ml of acetonitrile for 30 minutes, and the reaction mixture was worked up to yield 40 gm of the compound of the formula

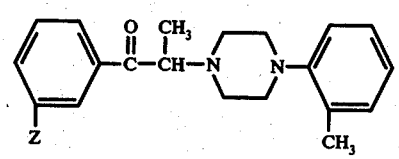

(m.p. 157° C).

6 gm of this aminoketone in 60 ml of ethanol were mixed with 1 gm of NaBH$_4$, and the mixture was heated to 50° C. After cooling, 1 gm of NaBH$_4$ was again added. 5 gm of the threo-form of compound E (m.p. 204° C) crystallized after about one hour. M.P. of its methane sulfonate: 241° C.

To prepare the erythro-form of compound E, 6 gm of the aminoketone were dissolved in methanol and hydrogenated with palladium/charcoal at 60° C and 5 atmospheres gauge. Working up yielded the erythro-form of compound E, m.p. 161° C.

EXAMPLE 26

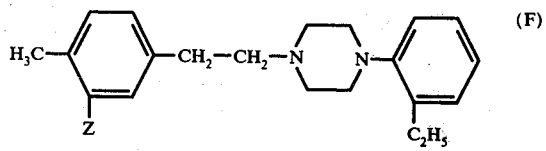 (F)

5 gm of the compound of the formula

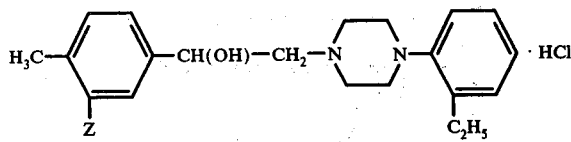 · HCl were added portionwise to 20 ml of thionyl chloride; the resulting solution turned red after some time. The excess thionyl chloride was distilled off, and the residue was brought to crystallization by the addition of acetonitrile and boiling. 3.3 gm of the compound of the formula

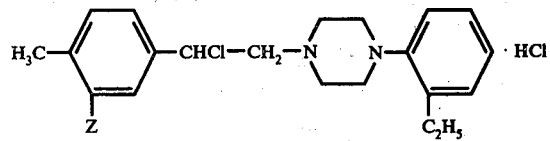 · HCl where thereby obtained, which were hydrogenated in the presence of 1.67 gm of dimethylaniline and Raney nickel as the catalyst in methanol until the absorption of hydrogen ceased. After removal of dimethylaniline by distillation, compound F was isolated from the residue as its hydrochloride, m.p. 256°–257° C.

The following compounds were prepared in analogous manner:

(1) 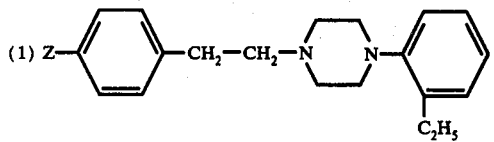

(2) 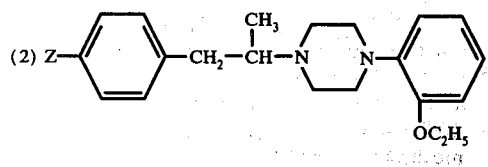

EXAMPLE 27

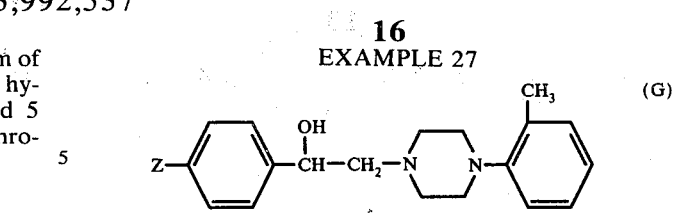 (G)

4-Amino-acetophenone was converted into 4-[imidazolidinon-(2')-yl]-acetophenone (m.p. 208° C) by reaction with β-chloroethyl-isocyanate, followed by treatment with potassium hydroxide. The ω-bromoketone of the formula

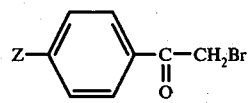

was obtained in chloroform by the addition of 1 mol of bromine. M.p. 175° C.

2 gm of sodium borohydride were slowly added to 14.2 gm of the bromoketone in 200 ml of ethanol while cooling with ice, and the reaction mixture was then stirred for two hours at room temperature. Precipitated sodium bromide was removed by vacuum filtration, 0.5 ml of water and 17.6 gm of N-2-methylphenylpiperazine were added to the filtrate, and the mixture was left to stand overnight at room temperature and was then refluxed for two hours. Compound (G) was then isolated; it had a melting point of 221°–223° C.

EXAMPLE 28

N-[4-Imidazolidinon-(2)-yl-phenylmethyl]-N'-phenyl-piperazine

N-Phenyl-N'-(4-nitro-benzyl)-piperazine was prepared from 4-nitro-benzyl bromide and N-phenyl-piperazine by refluxing in acetonitrile. Reduction of this compound with hydrogen/PtO₂ in methanol yielded N-phenyl-N'(4-aminobenzyl)-piperazine (m.p. 105° C), which was reacted with β-chloroethyl-isocyanate in benzene to yield the compound of the formula

C₁—CH₂—CH₂—NH—CO—NH

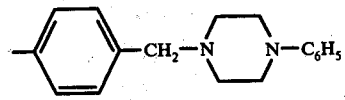

21 gm of this compound were mixed with 2.4 gm of NaOH in 160 ml of ethanol, and the mixture was refluxed for 10 minutes. 16 gm of the compound named in the heading of this example were obtained by isolation from ethanol (m.p. 218° C). Its methanesulfonate (m.p. 210° C) was obtaind from the base with the calculated quantity of methanesulfonic acid in ethanol.

The following compounds were prepared in analogous manner:

(1) 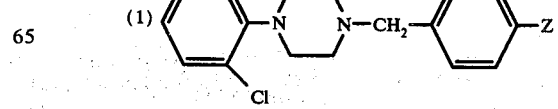

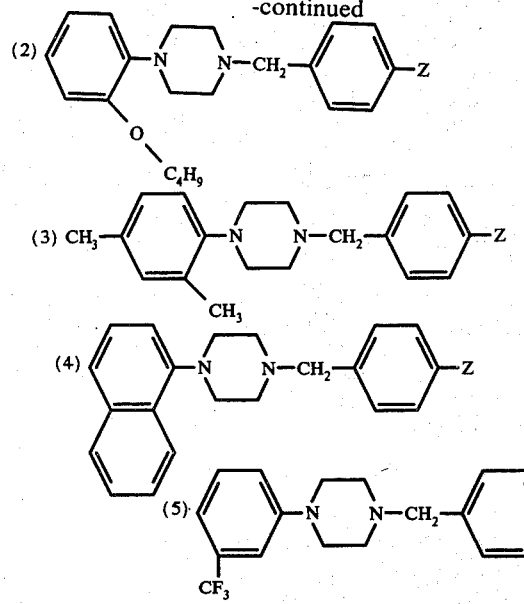

The compounds embraced by formula I and their nontoxic, pharmacologically acceptable acid addition salts, in both the optically inactive and optically active forms, have useful pharmacodynamic properties. More particularly, they exhibit CNS-depressing, neuroleptic, and anti-cholesteremic activities in warm-blooded animals, such as mice, rats, guinea pigs, dogs and cats.

Particularly effective are, inter alia, N-[4''-imidazolidinon-(2')-yl-phenethyl]-N'-(o-ethyl-phenyl)-piperazine and N-[4''-imidazolidinon-(2')-yl-phenethyl]-N'-(o-methyl-phenyl)-piperazine.

For pharmaceutical purposes the compounds of the formula I or their non-toxic acid addition salts are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, aerosols, suppositories and the like. One effective dosage unit of the compounds according to the present invention is from about 0.026 to 1.35 mgm/kg body weight, preferably from 0.666 to 0.67 mgm/kg body weight.

The following examples illustrate a few pharmaceutical dosage unit compositions comprising a compound of the formula I or a non-toxic acid addition salt thereof as an active ingredient and represent the best modes contemplated of putting the invention into practical use. The parts are parts by weight unless otherwise specified.

EXAMPLE 29

Tablets

The tablet composition is compounded from the following ingredients:

| | | |
|---|---|---|
| N-[4''-Imidazolidinon-(2')-yl-phenethyl] -N'-(o-ethyl-phenyl)-piperazine | 30 | parts |
| Lactose | 70 | '' |
| Corn starch | 93 | '' |
| Secondary calcium phosphate | 47 | '' |
| Soluble starch | 3 | '' |
| Magnesium stearate | 3 | '' |
| Colloidal silicic acid | 4 | '' |
| Total | 250 | parts |

Preparation

The piperazine compound is intimately admixed with the lactose, the corn starch and the calcium phosphate, the mixture is granulated with the aid of an aqueous solution of the soluble starch in conventional fashion, and the granulate is dried and admixed with the remaining ingredients. The composition is compressed into 250 mgm-tablets in a conventional tablet making machine. Each tablet contains 30 mgm of the piperazine compound and is an oral dosage unit composition with effective CNS-depressing action.

EXAMPLE 30

Coated pills

The pill core composition is compounded from the following ingredients:

| | | |
|---|---|---|
| N-[4''-Imidazolidinon-(2')-yl-phenethyl] -N'-(o-methyl-phenyl)-piperazine . HCl | 40 | parts |
| Lactose | 50 | '' |
| Corn starch | 80 | '' |
| Secondary calcium phosphate | 50 | '' |
| Magnesium stearate | 3 | '' |
| Soluble starch | 3 | '' |
| Colloidal silicic acid | 4 | '' |
| Total | 230 | parts |

Preparation

The ingredients are compounded in the same manner as in the preceding example, the composition is compressed into 230 mgm-pill cores which are subsequently coated with a thin shell consisting essentially of a mixture of talcum, sugar and gum arabic, and the coated pills are polished with beeswax. Each pill contains 40 mgm of the piperazine compound and is an oral dosage unit composition with effective CNS-depressing action.

EXAMPLE 31

Suppositories

The suppository composition is compounded from the following ingredients:

| | | |
|---|---|---|
| N-[4''-Imidazolidinon-(2')-yl-phenethyl] -N'-(m-chloro-phenyl)-piperazine . CH$_3$SO$_3$H | 30 | parts |
| Lactose, powdered | 45 | '' |
| Suppository base (e.g. cocoa butter) | 1625 | '' |
| Total | 1700 | parts |

Preparation

The lactose and the piperazine compound are intimately admixed with each other, the mixture is homogeneously blended into the molten suppository base, and 1700 mgm-portions of the composition are filled into cooled suppository molds and allowed to harden therein. Each suppository contains 30 mgm of the piperazine compound and is a rectal dosage unit composition with effective CNS-depressing action.

Analogous results are obtained when any one of the other N-phenyl-imidazolidinones embraced by formula I or a non-toxi salt thereof was substituted for the particular N-phenyl-imidazolidinone in Examples 29 through 31. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A CNS-depressing pharmaceutical dosage unit composition consisting essentially of an inert pharmaceutical carrier and an effective CNS-depressing amount of a compound of the formula

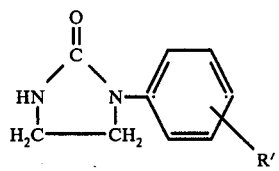

wherein
R' is in the m- or p-position and is selected from the group consisting of
—CH₂—A,
—CHR1—CH2—A
and

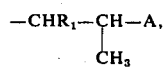

where
R₁ is hydrogen or hydroxyl, and
A is

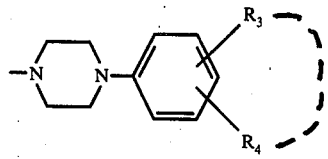

where
R₃ is hydrogen, chlorine, methyl, ethyl, trifluoromethyl or lower alkoxy, and
R₄ is hydrogen or methyl, or
R₃ and R₄, together with each other and neighboring carbon atoms of the phenyl ring to which they are attached, are naphthyl,
or a non-toxic, pharmacologically acceptable acid addition salt thereof.

2. A pharmaceutical composition of claim 1, wherein R' is selected from the group consisting of
—CH₂—A, —CHR₁—CH₂—A
and

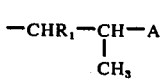

where
R₁ i hydrogen or hydroxyl, and
A is

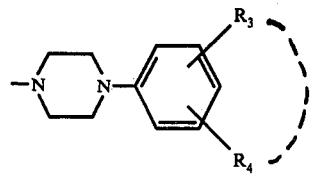

where
R₃ is hydrogen, chlorine, methyl or ethyl, and
R₄ is hydrogen or methyl, or
R₃ and R₄, together with each other and neighboring carbon atoms of the phenyl ring to which they are attached, and naphthyl.

3. A pharmaceutical composition of claim 1 where R' is selected from the group consisting of
—CH₂—CH₂—A
and

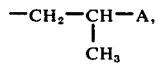

where A is

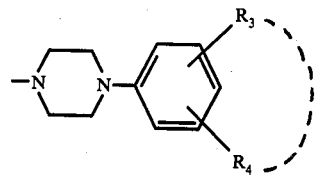

where
R₃ is hydrogen, chlorine, methyl or ethyl, and
R₄ is hydrogen or methyl, or
R₃ and R₄, together with each other and neighboring carbon atoms of the phenyl ring to which they are attached, are naphthyl.

4. A composition of claim 1, wherein said compound is N-[4''-imidazolidinon-(2')-yl-phenethyl]-N'-(o-ethylphenyl)-piperazine or a non-toxic, pharmacologically acceptable acid addition salt thereof.

5. A composition of claim 1, wherein said compound is N-[4''-imidazolidinon-(2')-yl-phenethyl]-N'-(o-methylphenyl)-piperazine or a non-toxic, pharmacologically acceptable acid addition salt thereof.

6. The method depressing the central nervous system of a warm-blooded animal in need of such treatment, which comprises perorally or parenterally administering to said animal an effective CNS-depressing amount of a compound of the formula

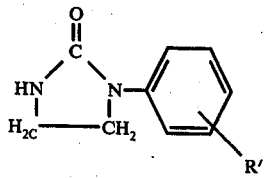

wherein
R' is in the m- or p-position and is selected from the group consisting of —CH2—A,
—CHR₁—CH₂—A
and

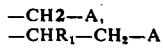

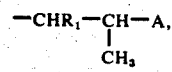

where R₁ is hydrogen or hydroxyl, and A is

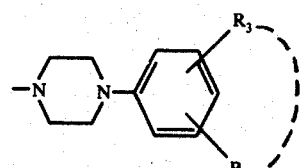

where
R₃ is hydrogen, chlorine, methyl, ethyl, trifluromethyl or lower alkoxy, and
R₄ is hydrogen or methyl, or
R₃ and R₄, together with each other and neighboring carbon atoms of the phenyl ring to which they are attached, are naphthyl,
or a non-toxic, pharmacologically acceptable acid addition salt thereof.

7. The method of claim 6, where R' is selected from the group consisting of

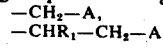
and

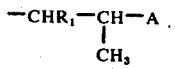

where
R₁ is hydrogen or hydroxyl, and
A is

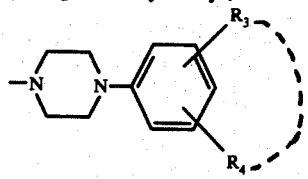

where
R₃ is hydrogen, chlorine, methyl or ethyl, and
R₄ is hydrogen or methyl, or
R₃ and R₄, together with each other and neighboring carbon atoms of the phenyl ring to which they are attached, are naphthyl.

8. The method of claim 6, where R' is selected from the group consisting of

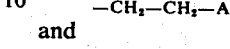
and

—CH₂—CH—A,
       |
      CH₃ where
A is

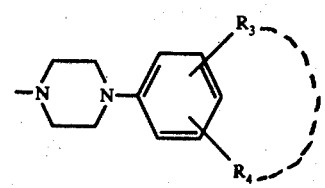

where
R₃ is hydrogen, chlorine, methyl or ethyl, and
R₄ is hydrogen or methyl, or
R₃ and R₄, together with each other and neighboring carbon atoms of the phenyl ring to which they are attached, are naphthyl.

9. The method of claim 6, wherein said compound is N-[4''-imidazolidinon-(2')-yl-phenethyl]-N'-o-ethyl-phenyl-piperazine or a non-toxic, pharmacologically acceptable acid addition salt thereof.

10. The method of claim 6, wherein said compound is N-[4''-imidazolidinon-(2')-yl-phenethyl]-N'-(o-methyl-phenyl)-piperazine or a non-toxic, pharmacologically acceptable acid addition salt thereof.

* * * * *

UNITED STATES PATENT OFFICE
CERTIFICATE OF CORRECTION

Patent No. 3,992,537                         Dated November 16, 1976

Inventor(s) Anton Mentrup et al.

It is certified that error appears in the above-identified patent and that said Letters Patent are hereby corrected as shown below:

Col. 3, line 22             "h-x-" should read -- H-X --

Col. 3, formulas III        "HN" should read  -- HN --
        and IV                                    |
                             |                   $H_2C$—
                            $H_2C$—

Col. 4, formulas VI         "HN" should read  -- HN --
        VII and VIII                              |
                             |                   $H_2C$—
                            $H_2C$—

Col. 4, formula VII         "N" should read -- N --
                                                  |
                            $CH_2$               $CH_2$ Col. 14, line 1             After "compound" insert -- D --

Signed and Sealed this

Sixth Day of December 1977

[SEAL]

Attest:

RUTH C. MASON
*Attesting Officer*

LUTRELLE F. PARKER
*Acting Commissioner of Patents and Trademarks*